United States Patent
Young et al.

(12)

(10) Patent No.: US 6,514,933 B1
(45) Date of Patent: Feb. 4, 2003

(54) PROCESS FOR THE PRODUCTION OF A FLAVOR OR A FRAGRANCE FORMULATION AS WELL AS AN ELECTRONIC DATA PROCESSING SOFTWARE PROGRAM

(75) Inventors: Timothy Jay Young, Atlantic Highlands, NJ (US); Michael J. Incorvia, Marlboro, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/573,533

(22) Filed: May 19, 2000

(51) Int. Cl.[7] ............................. A61K 7/46; G01N 31/16
(52) U.S. Cl. .............................. 512/1; 436/20; 436/24; 436/164; 436/55; 436/163; 426/665; 426/442
(58) Field of Search .......................... 512/1; 436/20–24, 436/164, 55, 163; 426/665, 442

(56) References Cited

PUBLICATIONS

Internet site of Protein Solutions, Inc. of 1224 West Main Street, Suite #777, Charlottesville, Virginia 22903 entitled "What's New/Products/Applications/ Online Support/Support Forum/Literature Ref5/FAQ's/Newsletter/Contact us/Search Site" (http://www.protein–solutions.com) (2000).

*Primary Examiner*—Jill Warden
*Assistant Examiner*—Monique T. Cole
(74) *Attorney, Agent, or Firm*—Arthur L. Liberman (57) ABSTRACT

Described is a process and electronic data processing software program for carrying out same, for the creation of a flavor or fragrance formulation or for the determination of the use of a fragrance or flavor ingredient in a fragrance or flavor formulation or use thereof in or on a perfume composition, perfumed article, cologne, foodstuff, beverage, oral care product (e.g., mouthwash) and/or chewing gum. The process uses apparatus which is a laser light beam transmitter fitted with a light scattering means having attached thereto a titration means.

19 Claims, 6 Drawing Sheets

PROCESS FOR THE PRODUCTION OF A FLAVOR OR A FRAGRANCE FORMULATION AS WELL AS AN ELECTRONIC DATA PROCESSING SOFTWARE PROGRAM

BACKGROUND OF THE INVENTION

Our invention is directed to a process and electronic data processing software program for carrying out same, for the creation of flavor or fragrance formulations or for the determination of the use of a flavor or fragrance ingredient in a flavor or fragrance formulation or a use thereof in or on a perfume composition, perfumed article, cologne, foodstuff, beverage, oral care composition and/or chewing gum where the flavor or fragrance formulation or ingredient have a particular and desired solubility in a solvent such as water.

The process is carried out using apparatus which is a laser light beam transmitter fitted with a light scattering means and having attached thereto titration means.

The use of automatic titrators for the investigation of such protocols such as water treatment protocols concerning ascertaining how zeta potential changes with the addition of charged salts can improve flocculation procedures is disclosed in the brochure entitled *THE ZETASIZER RANGE AUTOMATED DISPERSION TECHNOLOGY SOLUTIONS*, published by Malvern Instruments Inc. of 10 Southville Road, Southborough, Mass. 01772. Furthermore, a brochure entitled *DynaPro Dynamic Light Scattering Results Summary*, published by Protein Solutions discloses the theory overview and data implementation of dynamic light scattering apparatus whereby monochromatic laser light passes through a solution of non-interacting molecules and the fluctuation and scattered intensity caused by molecules or particles moving in Brownian motion is measured. The speed at which the molecules move is indicated to be inversely related to their size, and it is disclosed in the Protein Solutions publication that the parameter measured is known as the Translational Diffusion Coefficient (Dt) whereby the apparent Hydrodynamic Radius (Rh) of the particles can then be calculated with known temperature and solvent viscosity. The scattered light passes through a photo detector and photon correlator and computer equipped with electronic data processing software for ascertaining particle size.

Nothing is set forth in the Protein Solutions brochure or in the Malvern Instruments brochure disclosing a process for the creation of a fragrance or flavor formulation or ascertainment of the use of a fragrance or flavor ingredient in a fragrance or flavor formulation or a use thereof in a fragrance composition, perfumed article, cologne, foodstuff, beverage, oral care composition or chewing gum, wherein the flavor or fragrance ingredient or flavor or fragrance formulation has predicted solvent solubility.

It is well known that a need exists for the ability to create, on an industrial scale, flavor or fragrance compositions which have a defined and predictable solubility in a solvent such as water so that such flavor or fragrance formulations can be utilized in aqueous compositions or in aqueous systems such as liquid fabric softener compositions, liquid detergent compositions, detergents which are powdered which come in contact with large amounts of water such as in washing machines, powdered fabric softeners or fabric softener tablets which come in contact with large amounts of water during the washing machine procedure and the like.

Nothing in the prior art, however, discloses a technique for fulfillment of the above-stated need.

THE INVENTION

Our invention sets forth a process and electronic data processing software program for carrying out same, for the creation of a flavor or fragrance formulation or for the determination of the use of a fragrance or flavor ingredient in a fragrance or flavor formulation or use thereof in or on a perfume composition, perfumed article, cologne, perfumed polymer, foodstuff, beverage, oral care product (e.g., mouthwash or toothpaste) and/or chewing gum.

The process of our invention effects the determination of solvent solubility of such materials thereby enabling the use of such materials in solvent (e.g., water) systems.

Such water systems are affiliated with washing procedures such as those carried out in the process of washing fabrics and the like.

The process of our invention uses, inter alia, apparatus which is a laser light beam transmitter fitted with a light scattering means, for example, the DynaPro-LSR Molecular Sizing Instrument manufactured by Protein Solutions, Inc. of 1224 West Main Street, Suite #777, Charlottesville, Va. 22903. In carrying out the process of our invention, such laser light beam transmitter fitted with light scattering means has attached thereto a titration means consisting of two burettes:

(a) a "sample" burette holding one or more flavor or fragrance ingredients or a fragrance or flavor formulation; and (b) a "titrant" burette holding a solvent such as water.

The burettes may also contain gelatin and/or a surfactant such as didecylammonium chloride.

The purpose of the surfactant is for the formation of micelles containing flavor or fragrance or flavor formulation or fragrance formulation. The use of the gelatin is to form encapsulated flavor or fragrance oils or flavor formulation or fragrance formulation oils which are encapsulated with a hard gelatin shell formed by means of coacervation as a result of the gelatin precipitating around globules of flavor or fragrance or flavor formulation or fragrance formulation oil formed at the "endpoint" of the titration.

In general the surfactant useful in the practice of our invention are of the formula:

wherein $R_1$ and $R_2$ are the same or different $C_5$–$C_{20}$ alkyl, alkenyl, alkadienyl aryalkyl, alkarylalkyl, aryalalkyl and alkatrienyl for example, n-decyl, n-undecyl phenylethyl, phenylpropyl and o-ethylphenyl n-propyl. More specifically, a preferred surfactant is the dicecylammonium chloride having the structure:

In the foregoing generic structure, to wit:

X represents halogen, e.g., chloro, bromo or iodo; or X represents hydroxyl.

The solvent and fragrance or flavor ingredient or flavor or fragrance formulations are automatically titrated into the light scattering means where a dynamic titrant/sample mixture is formed proximate a monitoring device. When using gelatin, coacervation of the gelatin around the fragrance or flavor microdroplet takes place first forming microcapsules and then enlarging same during the titration procedure. The formation of the microdroplets takes place during the titration at the "endpoint" when the single phase liquid mixture reaches a point where the phases separate and microdroplets of flavor or fragrance ingredient or flavor or fragrance formulation form. At this "endpoint," very shortly after formation of the microdroplets, coacervation of the gelatin contained in the solution occurs whereby the gelatin comes out of solution and coacervates around the microdroplets.

When using a surfactant, fragrance micelles are first formed and are then enlarged at the endpoint. The micelles, which are formed, are formed as a result of the presence of surfactant at the endpoint of the titration. At the end point of the titration when the micelles are formed, microdroplets of flavor or fragrance ingredient or flavor or fragrance formulation are first formed followed by formation of the micelles.

Thus, the titration proceeds to a detectable endpoint where (i) single aqueous phase converts to a two phase particle/liquid phase system, e.g., a colloidal suspension or (ii) fragrance and flavor ingredient or flavor and fragrance formulation micelles or microcapsules are formed in the system and then enlarged.

Monitoring for the endpoint appearance, using specially designed electronic data processing software as set forth in detail, infra, will yield information concerning particle dimensions (e.g., hydration diameter) and will then yield water solubility data using derived algorithms, also as described in detail, infra.

More specifically, our invention provides a process for the creation of a fragrance or flavor formulation or ascertainment of the use of a flavor or fragrance ingredient in a fragrance formulation or use thereof on or in a foodstuff, beverage, chewing gum or oral care formulation or in a perfumed article, perfume composition, cologne, perfumed polymer or fragrance composition having predictable solvent solubility (for example, water solubility), comprising the steps of:

(i) providing a laser light beam transmitter fitted with a laser light scattering means;

(ii) providing a titration means upstream from and cooperating with said laser light scattering means consisting of two injection means (e.g., burettes), a first "titrant" injection means containing a solvent (e.g., water) and a second "sample" injection means containing a flavor or fragrance formulation or flavor or fragrance ingredient, with each of said injection means being connected to fluid transmission means (e.g., tubes) for transmitting and mixing said titrant with said sample in order to create a "dynamic titrant/sample mixture in the liquid phase";

(iii) continuously transporting said dynamic/titrant sample mixture through said laser light scattering means while substantially simultaneously (a) titrating said dynamic/titrant sample mixture to a solvent solubility endpoint and (b) monitoring said dynamic/titrant sample mixture in order to ascertain the dimensions of particles or globules formed or enlarged while said dynamic/titrant sample mixture is being transported within said laser light scattering means.

The foregoing process can also utilize a mixture in the sample means of surfactant and fragrance or flavor ingredient or flavor or fragrance formulation; and in the titrant means, water. In such a situation, the endpoint is represented by the formation of micelles and the enlargement of such micelles.

In monitoring the micelles when in contact with water, an enlargement of the micelles will be quantitatively a function of the solubility of the flavor ingredient or the fragrance ingredient or the flavor formulation or the fragrance formulation in the solvent, for example, water. Such a relationship between the solubility in water of the "sample" and the degree of enlargement of the microparticle, e.g., the micelle in this case, is governed according to the algorithm:

$$F_{SAT} = \frac{k_2}{k_1 k_3} e^{k_2 \theta} \left[\frac{\partial W}{\partial \theta}\right] - 4\pi R^2 \left[\frac{\partial R}{\partial \theta}\right]$$

wherein $k_1$, $k_2$ and k3 are constants; wherein the symbol $\theta$ is representative of time; wherein R is globule radius; wherein the term $$\left[\frac{\partial R}{\partial \theta}\right]$$

represents the rate of change of the radius of the globule or microparticle with respect to time; wherein the term $$\left[\frac{\partial W}{\partial \theta}\right]$$

represents the rate of water entry into the globule with respect to time or the rate of solvent entry into the globule or microparticle with respect to time; and wherein the term $F_{SAT}$ represents the saturation level for the "sample" that is, for the fragrance ingredient or flavor ingredient or fragrance formulation or flavor formulation previously located in the sample means.

The foregoing algorithm is used in conjunction with the following algorithm:

$$g(\theta) = p(\Gamma) \left\{ e^{\left(-\frac{2}{3}\frac{KT\theta[8\pi n^2 \sin^2[\frac{\alpha}{2}]]}{3\eta R \lambda^2}\right)} \right\}$$

wherein the term g($\theta$) represents the normalized intensity correlation function; the symbol $\lambda$ represents the scattered light wave length; the symbol $\alpha$ represents the scattering angle; the symbol $\eta$ represents the solvent viscosity; the symbol T represents temperature (absolute degrees Kelvin); n is the refractive index of the sample, that is the fragrance ingredient or flavor ingredient or the fragrance formulation or the flavor formulation; K is the Boltzmann constant.

The aforementioned algorithm is derived from the following algorithms:

$$g(\theta) = [p(\Gamma)]e^{-2\Gamma\theta} + 1; \quad \Gamma = D_T q^2; \quad q = \frac{4\pi n}{\lambda}\sin\left(\frac{\alpha}{2}\right); \text{ and}$$

$$D_T = \frac{KT}{6\pi\eta R}.$$

wherein q is the scattering vector for the scattered light and $D_T$ is the translation diffusion coefficient.

In another embodiment of our invention, the titrant is a mixture of water and gelatin and the sample is a flavor or fragrance ingredient or a flavor or fragrance formulation; and the endpoint is represented by formation and enlargement of a coacervation wherein enlarged gelatin microcapsules containing fragrance ingredient or flavor ingredient or fragrance formulation or flavor formulation are formed.

The microcapsules initially have a radius R and on continued immersion in a solvent such as water, fragrance or flavor is evolved from the microcapsule into the solvent and, simultaneously, solvent, e.g., water, enters via osmosis each of the microcapsules causing the microcapsules to swell and causing the radius R to expand by an increment, $\Delta R$, whereby the final radius is shown by the term $R=R_0+\Delta R$ and wherein the increase of radius is also shown by the equation:

$$\Delta R = \int_0^\theta \left(\frac{\partial R}{\partial \theta}\right) d\theta.$$

The process of our invention also includes the additional step of using the solubility data generated from endpoint particle size or globule size data ascertained using the aforementioned algorithms to ascertain solvent-soluble fragrance ingredient or formulation or solvent-soluble flavor ingredient or formulation and then crafting said formulation utilizing the data.

The resulting formulations may then be added to colognes, perfumed polymers and perfumed articles (in the case of fragrance ingredients or fragrance formulations) or to foodstuffs, chewing gums, beverages or oral care products (in the case of fragrance ingredients or flavor formulations). Perfumed articles include but are not limited to solid or liquid anionic, cationic, nonionic or zwitterionic detergents, fabric softener compositions, fabric softener articles and hair care preparations including shampoos and bleach formulations.

In crafting the electronic data processing program software, the following steps are utilized in the practice of our invention:

1(a). ascertaining the nature of the light scattering material to be formed at the endpoint, e.g., microcapsule or micelle;
1(b). input of the data of 1(a) into memory;
2(a). establishment of the use of the ultimate flavor ingredient or flavor formulation or fragrance ingredient or fragrance formulation;
(2b). input of the data of 2(a) into memory;
3(a). establishment of constraints for:
 (i) flavor or fragrance ingredient or formulation aroma profile;
 (ii) fragrance or flavor ingredient or formulation profile on treated product (e.g., perfumed article); and
 (iii) total fragrance or flavor ingredient or formulation solvent solubility (e.g., water solubility);
3(b). input of constraints of 3(a) into memory;
4. effecting loading of titrant burette or syringe with solvent (e.g., water) and, optionally, coacervating material in given proportion to solvent;
5. effecting loading of sample syringe or burette with sample (e.g., fragrance ingredient or flavor ingredient or fragrance or flavor formulation) (and, optionally, in set proportions, surfactant and/or coacervating material);
6(a). setting system to reject solvent (e.g., water) solubility of sample (e.g., flavor or fragrance ingredient or formulation) below $S_A$, e.g., to wit: "reject if $S_i \leq S_A$" and "accept if $S_i > S_A$";
6(b). input data of 6(a) into memory;
7. engage light scattering apparatus;
8(a). simultaneously engage sample syringe or burette at rate $\rho_S$ and titrant injection burette at rate $\rho_T$ through microsampler whereby endpoint may be reached and ascertained causing solubility in solvent to be ascertained via automatic calculation using algorithms and indicating fragrance or flavor ingredient or formulation saturation level in solvent and relationship of such saturation level to globule or particle size or capsule or micelle size;
8(b). entry of output of 8(a) into memory;
9. is $S_i > S_A$, if so accept;
10. repeat steps 4 and 5, k times at $$\frac{k}{2}$$

different rates of $\rho_S$; and $$\frac{k}{2}$$

different rates of $\rho_T$; and $$\frac{k}{3}$$

different ratios of $\rho_S:\rho_T$ and $$\frac{k}{3}$$

different temperatures in order to develop means for $F_{SAT}$ of given temperatures; and for each repetition, repeat steps 6(a) and 6(b);
11. plot data for steps 5, 6(a), 10 and 11 and input to memory;
12. repeat steps 1–11 for m fragrance or flavor ingredients and formulations, $[F_1 F_2, \ldots F_{m-1}, F_m]$ wherein m is an integer of from 4 up to 100;
13. scan accepted data and formulate entire flavor and fragrance formulations based on data; and add to sample burettes for solubility determination. Set to accept if $[\Sigma S_i] > S_B$ and set to reject if $[\Sigma S_i] \leq S_B$ where S represents solubilities and $S_A$ and $S_B$ represent target solubilities with $S_i$ representing sample solubilities. [In each of the foregoing "acceptance" or "rejection" cases, prior to such acceptance or rejection, there is still a rejection if the endpoint is such that the fraction of samples and titrants committed are less than about 0.2, e.g., f<0.2 and acceptance if the fractions of sample and titrant are greater than or equal to 0.2, to wit, f≧0.2.]

[The formulations are carried out desirably at a "perfumer's workstation," "PWS."]

If the resultant materials are rejected from the perfumer's workstation, at this point the flavor or fragrance formulation is reworked and steps 1–7 are repeated; and 14. apply the resultant formulation to a substrate, e.g., perfumed article, such as a solid or liquid anionic, cationic, nonionic or zwitterionic detergent. The resultant product is either accepted or rejected based upon the aroma thereof as evaluated instantaneously and over a period of time. If, at this point, the sample is rejected, then the sample is reworked by repeating therefor steps 1–7.

DETAILED DESCRIPTION OF THE DRAWINGS

Figure 1:
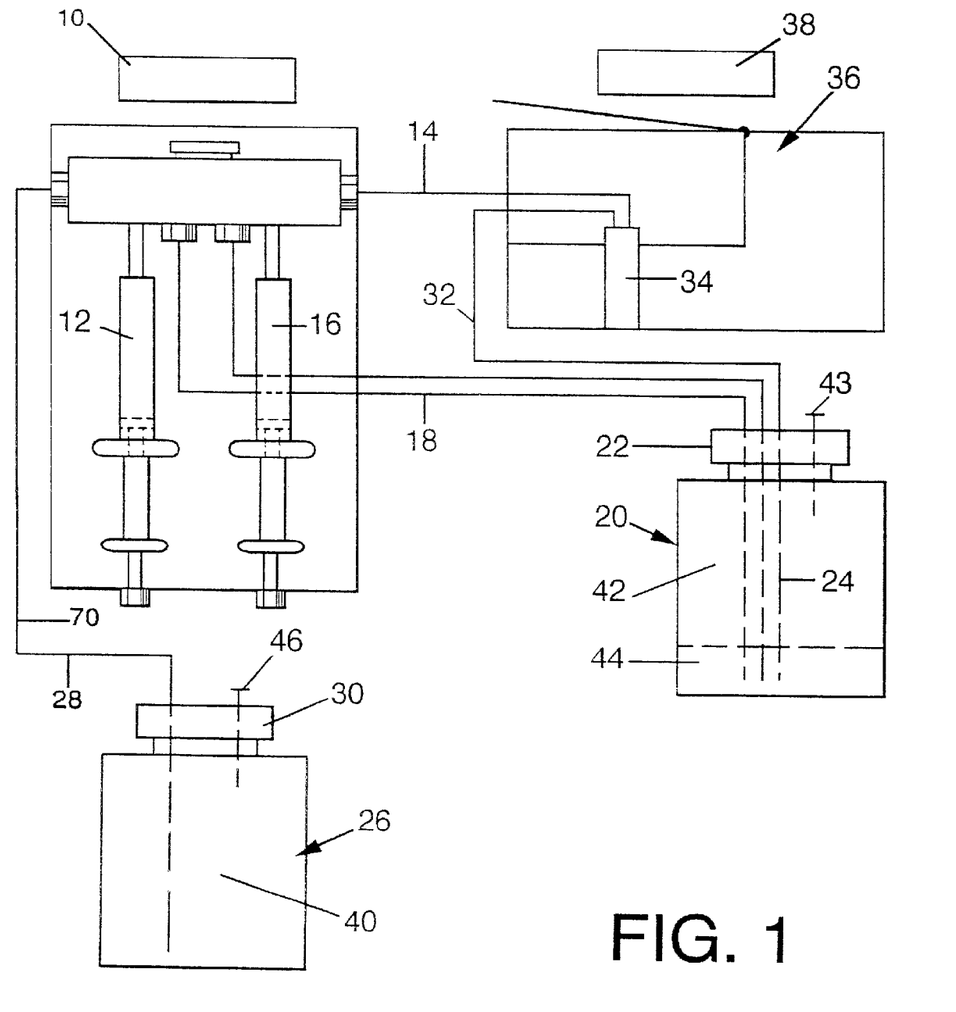
FIG. 1 is a schematic diagram of a laser light beam transmitter fitted with a laser light scattering means and provided with a titration means upstream from and cooperating with said laser light scattering means consisting of two injection means, a first "titrant" injection means containing a solvent and a second "sample" injection means containing a flavor or fragrance ingredient or formulation, useful in conjunction with the process of our invention.

Referring to FIG. 1, in the autotitrator represented by reference numeral 10, and upstream from the laser light beam transmitter which is fitted with a laser light scattering means, titrant injection syringe 12 is operated simultaneously with sample syringe pump 16 whereby the sample from syringe pump 16 is titrated against titrant (e.g., water) from syringe 12. Titrant passes through line 18 into reagent bottle 20 and then through line 32 into the low volume flow cell 34 located in optics block 36 of the laser light beam transmitter, e.g., DynaPro® MicroSampler indicated by reference numeral 38.

Sample, e.g., flavor or fragrance formulation or ingredient, passes through sample line 14 into low volume flow cell 34, simultaneously, and the sample and titrant are mixed at location 34 in order to create, at a given point in time, a mixture which represents the "endpoint" of the titration showing formation of microglobules, microparticles, coacervates (e.g., microcapsules) or micelles. The reagent bottle 20 is fitted with a 4-line sample bottle cap 22 in addition to a line communicating with a nitrogen tank in order to maintain a nitrogen blanket over the ingredients contained therein indicated by reference numeral 43. Simultaneously, reagent bottle 26 having an inner void 40 and equipped with vent plug 46 feeds titrant injection syringe 12 by means of line 28. Preferably, line 32, communicating reagent bottle 20 with microsampler 38 and low volume flow cell 34, is equipped with threaded metal syringe tips 24. Reference numeral 44 indicates liquid inside the reagent bottle 20 and reference numeral 42 is indicative of the headspace in the reagent bottle 20 above the liquid 44.

Figure 2:
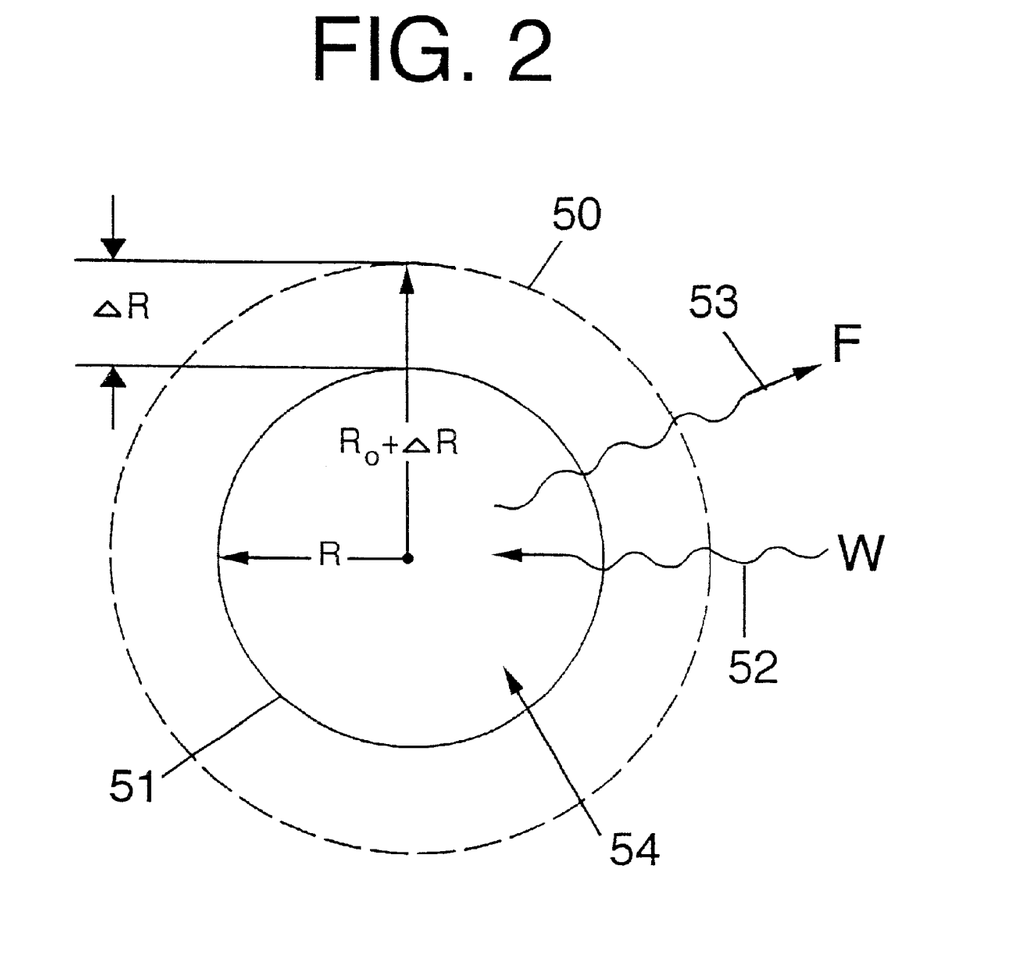
FIG. 2 is a schematic representation of a microglobule or microparticle or micelle or microcapsule containing flavor or fragrance ingredient or formulation as solvent enters said particle or globule or microcapsule or micelle and flavor or fragrance ingredient or formulation leaves said particle or globule or microcapsule or micelle simultaneously with the entry of solvent; while, simultaneously, the globule or particle or micelle or microcapsule size expands from $R_0$ to $R=R_0+\Delta R$.

Referring to FIG. 2, the original micelle, globule, microparticle or microcapsule is indicated by reference numeral 51 having radius R. Within such globule, microparticle, microcapsule or micelle is a fragrance or flavor ingredient or formulation indicated by reference numeral 54. On contact with solvent, fragrance ingredient or formulation or flavor ingredient or formulation F (indicated by reference numeral 53) diffuses through the wall of 51 while solvent W (indicated by reference numeral 52) back-diffuses (via osmosis) into the microcapsule or microglobule or micelle or microparticle while, simultaneously, the volume 54 increases such that $R=R_0+\Delta R$ at saturation, the outer wall wherein $R=_0+\Delta R$ is indicated by reference numeral 50.

Figure 3:
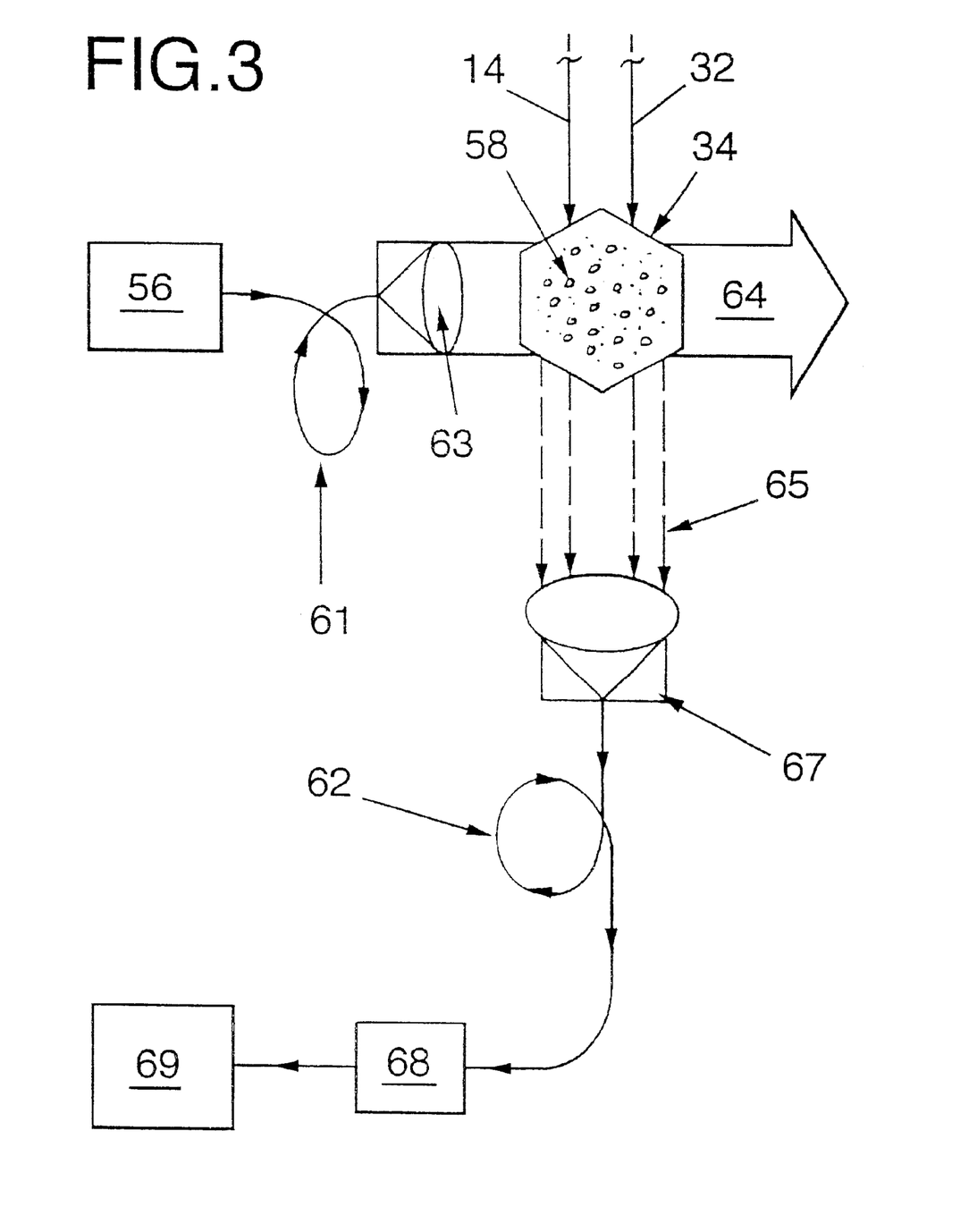
FIG. 3 is a schematic diagram in sequential flow form showing the laser light beam transmitter fitted with laser light scattering means and showing schematically entry into the laser light scattering section of the apparatus the sample and titrant from the titrating means located upstream from and cooperating with said laser light scattering means.

Referring to FIG. 3, laser means 56 transmits a laser beam through monomode optical fibers 61 into fiber beam transmitter 63 simultaneously, titrant enters light scattering means 58 through line 32 and sample enters light scattering means 58 through line 14 (shown in FIG. 1) where the mixing takes place in a low volume flow cell as shown in FIG. 1 as indicated by reference numeral 34. Part of the laser beam forms scattered light beams 65 with the remainder of the laser beam continuing on as indicated by reference numeral 64.

The scattered light 65 is then impacted upon fiber beam receiver 67 wherein it again forms a laser beam which travels through monomode optical fibers 62 into photo detector 68 and then into photo correlator and computer 69 wherein the microparticle, microglobule, micelle or microcapsule size is indicated as a function of the solubility of the flavor or fragrance ingredient or formulation by means of particular algorithms shown herein.

Figure 4:
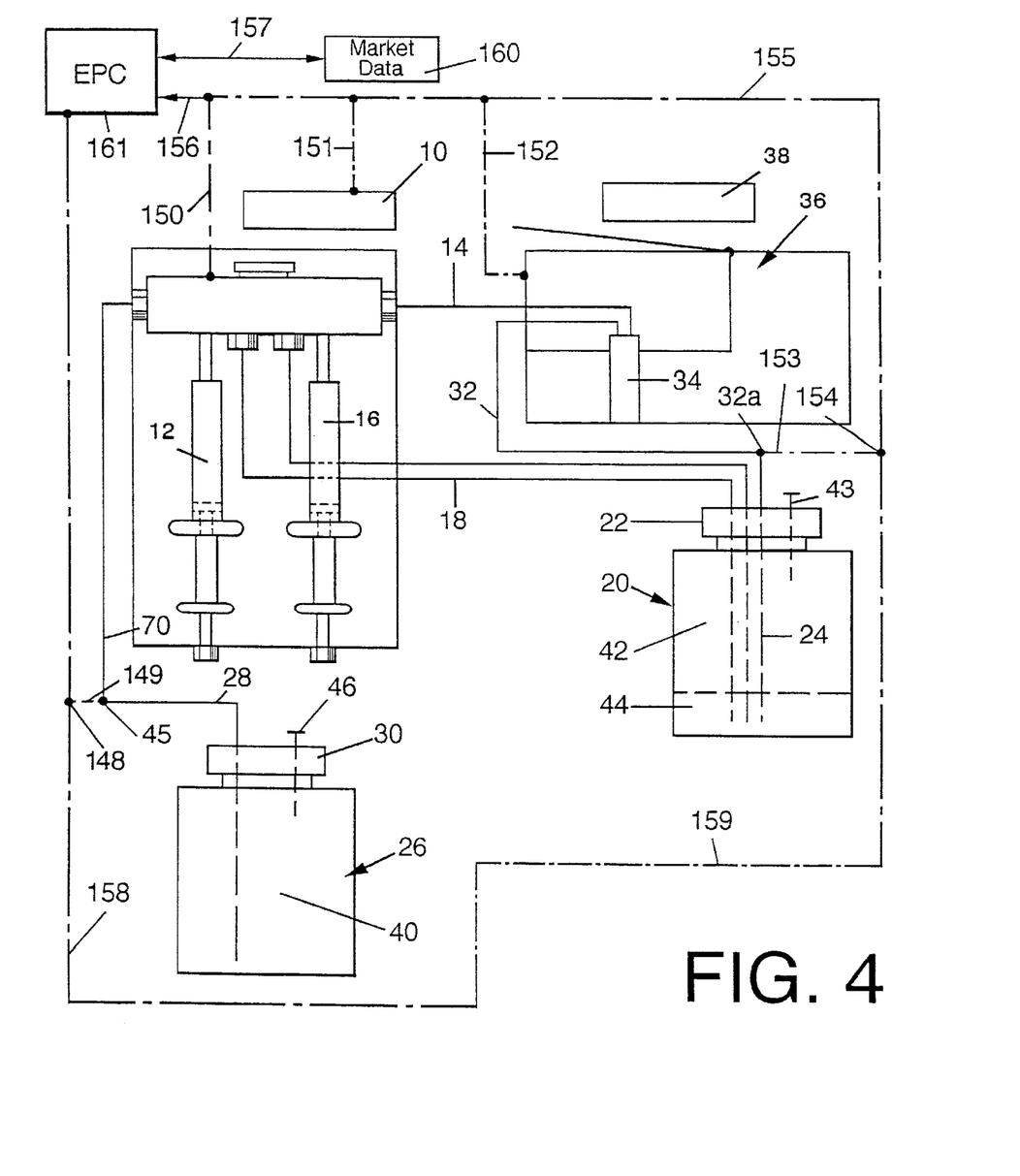
FIG. 4 sets forth the laser light beam transmitter fitted with laser light scattering means and being provided with a titration means upstream from and cooperating with said laser light scattering means, with the entire apparatus being monitored and controlled using electronic data programming systems and having marketing data applied thereto in order to optimize via appropriate algorithms, the output of the system, namely flavor or fragrance ingredients or flavor or fragrance formulations having set, desired solubilities in solvents such as water.

Referring to FIG. 4, the apparatus of FIG. 1 is controlled and monitored using electronic program controller 157 into which is fed marketing data from 160. Control lines 158/159/155/156 control the apparatus as follows (enabling the apparatus to operate the process of our invention): at junction 148 line 149 is connected to pump 4, directing titrant from reagent bottle 26 through line 28 into titrant injection syringe 12. At junction 154, via route 153 to pump 46, titrant via titrant line 18 is passed through reagent bottle 20 to line 32 and then into low volume flow cell 34 wherein sample is joined with titrant for the titration procedure. At junction 170 through line 152, the laser light beam transmitter fitted with a laser light scattering means is synchronized to operate with the titration means located upstream from and cooperating with said laser light scattering means. Such synchronization is also aided via line 151 through junction 172 and line 150 through junction 174. The market data from location 160 being fed into electronic program controller 157 is used to iterate the variables concerning the initial provision of sample into syringe pump 16 via lines 150 and 151 from junctions 172 and 174.

Figure 5:
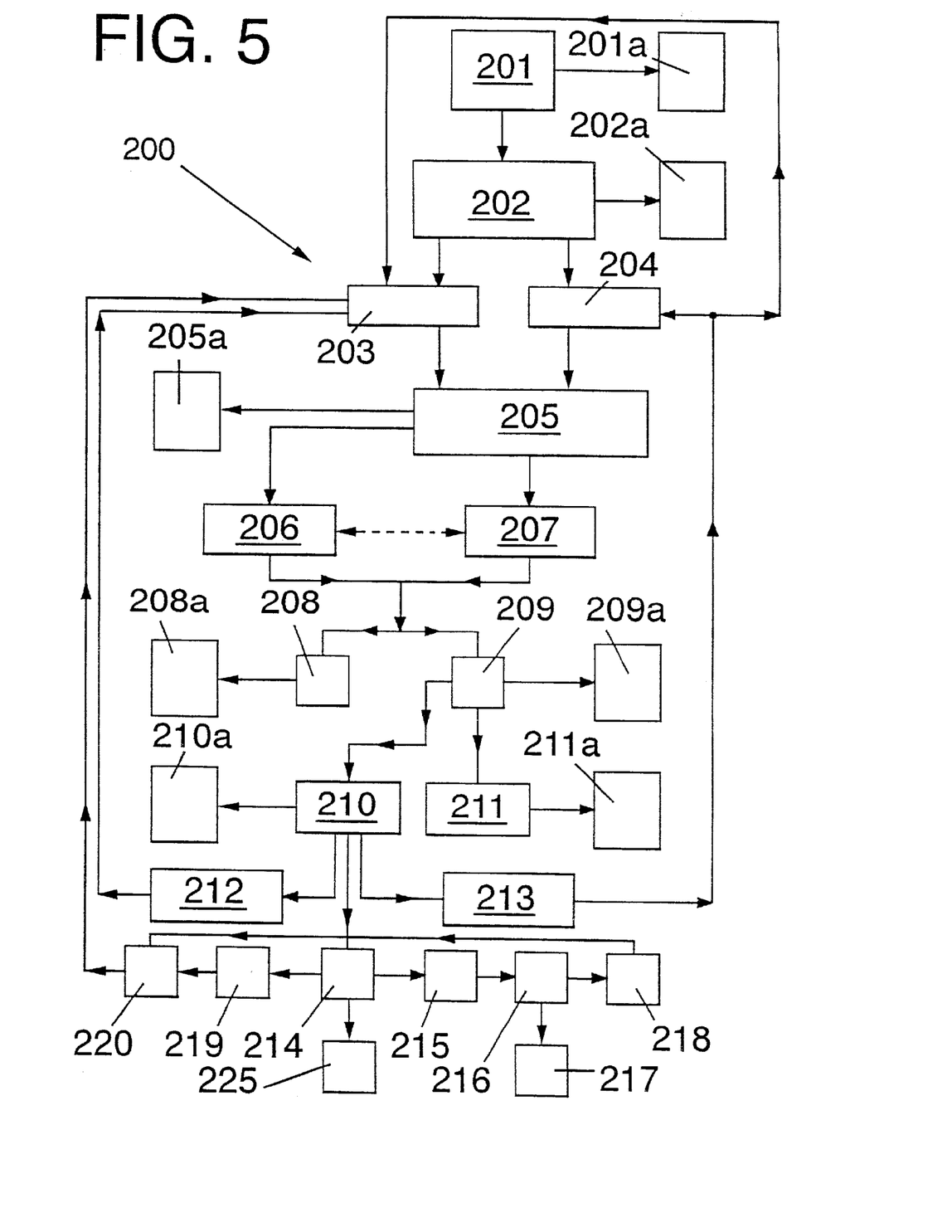
FIG. 5 is a schematic flow diagram indicating the use of electronic data processing program software in conjunction with the process of our invention for creation of a fragrance formulation having predictable solvent solubility.
Figure 6:
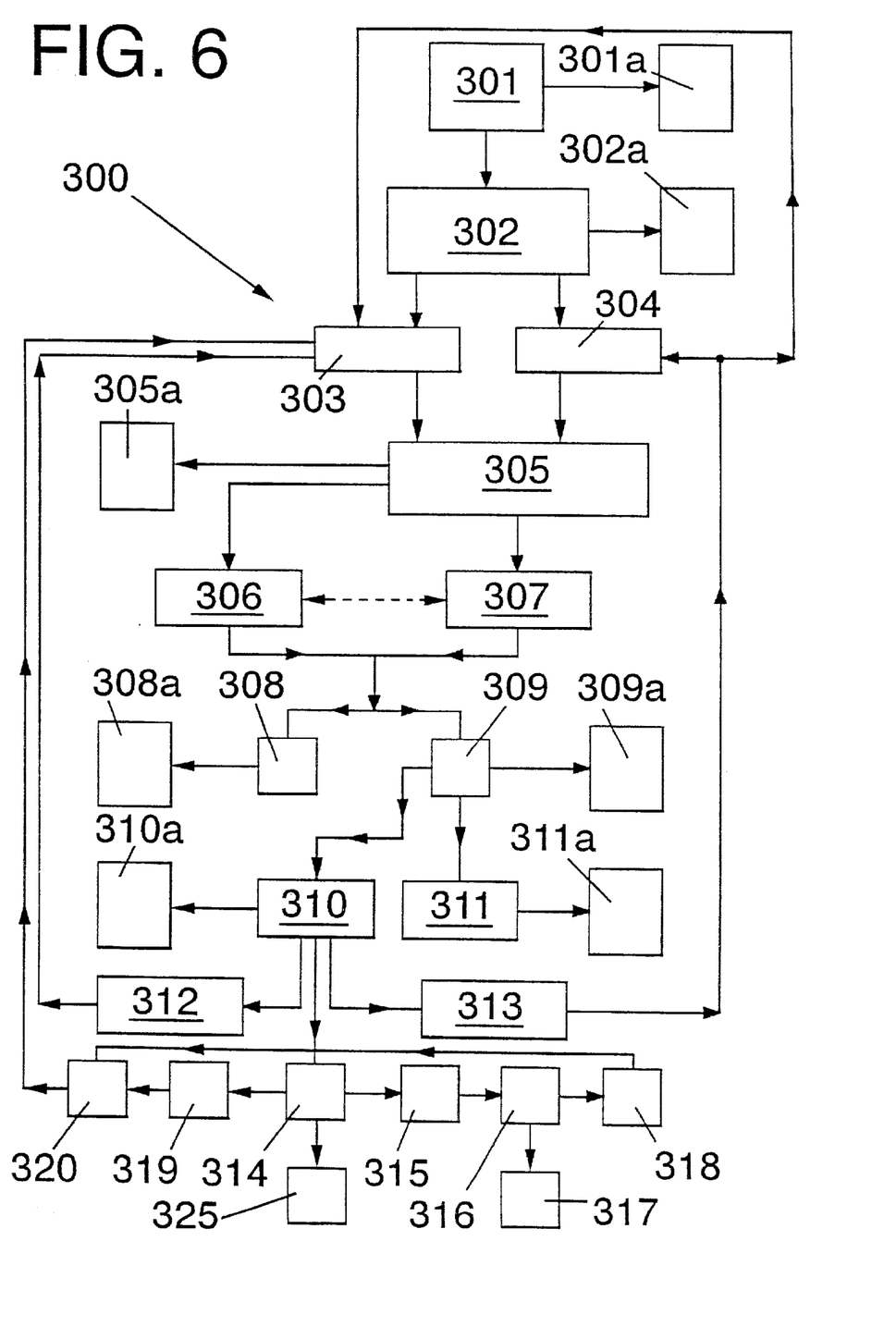
FIG. 6 is a schematic flow diagram indicating the use of electronic data processing program software in conjunction with the process of our invention for creation of a flavor formulation having predictable solvent solubility.

With reference to the electronic data processing program software shown in FIGS. 5 and 6, ascertainment of the nature of the light scattering material, e.g., fragrance ingredient or fragrance composition, is indicated by reference numeral 201 with input to memory thereof indicated by reference numeral 201a.

The overall program is indicated by reference numeral 200.

Reference numeral 202 indicates establishment of constraints for:

(i) fragrance aroma profile;
(ii) fragrance profile on treated product, e.g., perfumed article; and
(iii) total fragrance/water solubility with input to memory indicated by reference numeral 202a.

The operation of loading the sample syringe is indicated by reference numeral 203 and the operation of loading titrating material is indicated by reference numeral 204 wherein it is also shown that such materials are recycled for the repetition of different loading rates from location 213.

The setting of the system to reject ingredients having given water solubility, and to reject fragrance formulations having given water solubilities is set forth using reference numeral 205 with input to memory indicated by reference numeral 205a wherein the rejection of the fragrance ingredient or fragrance formulation is under the constraint: $S_i \leq S_A$; and the acceptance is under constraint: $S_i > S_A$; and wherein the rejection of an entire formulation is indicated by constraint: $[\Sigma S_i] \leq S_B$; and the acceptance of such formulation is indicated under constraint: $[\Sigma S_i] > S_B$. The engaging of the sample and titration syringes simultaneously with the engagement of laser light scattering apparatus is indicated, respectively, by reference numerals 206 and 207 where rejection of the product is indicated to occur at reference numeral 208, if the endpoint occurs with a fraction of the titrant and sample being less than 0.2, to wit: f<0.2, and acceptance is indicated if the fraction is greater than or equal to 0.2, to wit: f>0.2 at reference numeral 209. Input to memory for the rejection is indicated at reference numeral 208a, and input to memory for acceptance is indicated at reference numeral 209a. If acceptance exists at 209, then it follows that acceptance or rejection based on solubility occurs, respectively, at 210 and at 211, with acceptance occurring under the constraint: $S_i > S_A$ and rejection occurring under the constraint: $S_i \leq S_A$, with input to memory indicated at 210a for acceptance or 211a for rejection. Assuming acceptance at 210, repetition is instructed at 212 for different fragrances and at 213 for different loading rates, with repetition staring again at 203 for the 212 repetition and at 204 and 203 for the 213 repetition. Furthermore, assumption of acceptance at 210 gives rise to the carrying out of a test for total fragrance, aroma and solubility at 214, giving rise to rejection under the constraint: $[\Sigma S_i] \leq S_B$ indicated by reference numeral 225; acceptance, if odor acceptable and if within the constraint: $[\Sigma S_i] > S_B$ shown at location 215; and rejection, if not odor acceptable shown at location 219. If rejection based on odor inacceptability occurs at 219, then reformulation is instructed at location 220, with reformulation again staring at location 203 where instruction for loading sample syringe occurs. If acceptance occurs at 215, then fragrance functionality acceptability is questioned at location 216. If fragrance functionality is acceptable at 216, then the fragrance goes to market at 217, but if functionality is not acceptable, then instruction 218 is given where reformulation then occurs at 220, and the reformulation again begins at 203 where the sample syringe is loaded with sample for retitration and reevaluation.

By the same token, referring to FIG. 6, ascertainment of the nature of the light scattering material, to wit: flavor material or fragrance material or encapsulated flavor material (as by coacervation) or flavor materials which are micelles is indicated by reference numeral 301 with input to memory at 301a. The overall program is indicated by reference numeral 300.

Establishments of constraints for:

(i) flavor aroma profile;
(ii) flavor profile on treated product (e.g., foodstuff, chewing gum, beverage or oral care composition); and
(iii) total flavor/water solubility is indicated by reference numeral 302 with input to memory at 302a. Sample syringe loading occurs, after establishment of constraints, at reference numeral 303 where recycled material, based on repetition for different loading rates (at 313), also is inputted.

Titrating material is loaded simultaneously with sample syringe loading at 304, with input to the instruction for loading titrating material also coming from 313 where instruction for repeating of different loading rates is given after acceptance at 310.

Setting the system to reject flavor ingredients having given water solubility; and to reject flavor compositions having given water solubility is indicated at 305 with input to memory at 305a.

Simultaneous engagement of sample and titrant syringes and engagement of laser light scattering apparatus is indicated by reference numerals 306 and 307, respectively; where rejection, if the endpoint is at a fraction of titrant or sample of less than 0.2 is instructed at 308 with input to memory at 308a; and acceptance if endpoint exists at a fraction of titrant or sample of greater than or equal to 0.2 being at 309 with input to memory at 309a. Assuming acceptance at 309, then acceptance under the constraint: $S_i > S_A$ is instructed at 310 with input to memory at 310a; and rejection under the constraint: $S_i \leq S_A$ is indicated by reference numeral 311 with input to memory at 311a.

Assuming acceptance at 310, then instructions are given for repeating the process for different flavors at 312 and again repeating the procedure starting at 303 with the loading of the sample syringe, and instructions are given for repeating for different loading rates at 313 starting with loading titrating material at 304 and loading sample syringe at 303. Furthermore, assuming acceptance at 310, carrying out of actual tests for total flavor is instructed at 314, with a rejection instruction at 325 based on poor solubility properties under the constraint: $[\Sigma S_i] \leq S_B$ indicated by reference numeral 325. If flavor acceptable and under the constraint: $[\Sigma S_i] > S_B$, shown by reference numeral 315, the next instruction is determined by ascertaining whether the flavor functionality is acceptable in a chewing gum, beverage, oral care composition or foodstuff at reference numeral 316. If flavor functionality is acceptable, then the instruction "yes" is given for marketability at reference numeral 317. If not, then a rejection instruction is given at reference numeral 318 where reformulation occurs then at reference numeral 320. If reformulation occurs at reference numeral 320, the reformulation is begun again at the sample loading syringe point given by an instruction indicated by reference numeral 303. If after carrying out the actual test for total flavor at 314 an instruction for rejection is given at 319 as a result of flavor unacceptability, then the flavor is also reformulated at location 320 and an instruction is given to reload the sample syringe with a new flavor formulation after the reformulation occurs at 320, at 303.

The following example is illustrative, and the invention is only limited as set forth in the claims following said example.

EXAMPLE I

In the apparatus of FIG. 1:

(a) 0.8 cc of distilled water admixed with 0.2 grams of gelatin dissolved therein is added to titrant injection syringe 13 from reagent bottle 26 at 25° C.;

(b) 0.8 cc of a 50:50 mixture of coumarin and β-phenylethyl alcohol is added to the sample syringe pump 16 at 25° C.;

(c) the DynaPro® MicroSampler 38 is engaged with a laser beam impinging low volume flow cell 34;

(d) simultaneously, β-phenylethyl alcohol-coumarin mixture is titrated with the water-gelatin mixture until, at an initial endpoint, microcapsules averaging 6.8 microns in diameter are formed; and (e) after mixing with water for a period of 110 seconds, the average diameter of the microcapsules is 7.8 microns, yielding the "true endpoint."

Use of the algorithms:

$$g(\theta) = p(\Gamma) \left\{ e^{\left(-\frac{2}{3} \frac{KT\theta \left[8\pi n^2 \sin^2\left[\frac{\alpha}{2}\right]\right]}{3\eta R \lambda^2}\right)} \right\} \text{ and}$$

$$F_{SAT} = \frac{k_2}{k_1 k_3} e^{k_2 \theta} \left[\frac{\partial W}{\partial \theta}\right] - 4\pi R^2 \left[\frac{\partial R}{\partial \theta}\right]$$

(the terms of which are defined, supra) yields a 50:50 β-phenylethyl alcohol plus coumarin-water saturation solubility for the mixture β-phenylethyl alcohol-coumarin (50:50) of 0.05 gram moles per liter.

From the results obtained, 10 kilos of microcapsules are produced by means of coacervation of gelatin around a liquid 50:50 coumarin-β-phenylethyl alcohol center were prepared.

At the rate of 1%, the microcapsules were added to a nonfragranced, generic aqueous liquid household detergent purchased in Sainsbury's, Liverpool, United Kingdom.

The resulting detergent on use on polyester fabrics caused the fabrics, after washing and drying to have an aesthetically pleasing rose/fruit aroma. The aesthetically pleasing rose/fruit aroma is relatively substantive in that it is perceivable at substantially constant intensity for a 3 month period wherein the fabric was exposed to the washing/drying procedure 8 times at equal intervals over the 3 month period.

What is claimed is:

1. A process for the creation of a fragrance or flavor formulation or ascertainment of the use of a fragrance or flavor ingredient in a flavor or fragrance formulation or use thereof on or in a foodstuff, beverage, chewing gum, oral care composition, perfume composition, cologne, perfumed article or a perfumed polymer having predictable solvent solubility comprising the steps of:

(i) providing a laser light beam transmitter fitted with a laser light scattering means;

(ii) providing a titration means upstream from and cooperating with said laser light scattering means consisting of two injection means, a first "titrant" injection means containing a solvent and a second "sample" injection means containing a flavor or fragrance formulation or a flavor or fragrance ingredient, each of said injection means being connected to fluid transmission means for transmitting and mixing said titrant with said sample to create a dynamic titrant/sample mixture in the liquid phase;

(iii) continuously transporting said dynamic titrant/sample mixture through said laser light scattering means while substantially simultaneously (a) titrating said dynamic titrant/sample mixture to determine a solvent solubility endpoint and (b) monitoring said dynamic titrant/sample mixture in order to ascertain the dimensions of microparticles or globules or micelles or microcapsules formed or enlarged while said dynamic titrant/sample mixture is being transported within said laser light scattering means;

(iv) generating solubility data from said endpoint determination.

2. The process of claim 1 wherein the titrant is water and the sample is a mixture of surfactant and fragrance or flavor ingredient or formulation; and the endpoint is presented by the formation and enlargement of micelles.

3. The process of claim 1 wherein the dynamic titrant/sample mixture is initially a single phase mixture and the arrival of the endpoint is represented by the formation of a colloid containing microdroplets of fragrance or flavor formulation or fragrance or flavor ingredient.

4. The process of claim 1 wherein the titrant is a mixture of water and gelatin and the sample is a flavor or fragrance ingredient; and the endpoint is represented by formation and enlargement of a coacervate wherein enlarged gelatin microcapsules containing fragrance or flavor ingredient are formed.

5. The process of claim 1 comprising the additional step of adding the resulting formulation to a perfumed article base which is a liquid aqueous detergent base.

6. The process of claim 1 comprising the additional step of adding the resulting formulation to an aqueous beverage.

7. The process of claim 2 comprising the additional step of adding the resulting formulation to a perfumed article base which is a liquid aqueous detergent base.

8. The process of claim 3 comprising the additional step of adding the resulting formulation to a perfumed article base which is a liquid aqueous detergent base.

9. The process of claim 4 comprising the additional step of adding the resulting formulation to a perfumed article base which is a liquid aqueous detergent base.

10. The process of claim 1 which is governed by the algorithm:

$$g(\theta) = p(\Gamma) \left\{ e^{\left(-\frac{2}{3} \frac{KT\theta \left[8\pi n^2 \sin^2\left[\frac{\alpha}{2}\right]\right]}{3\eta R \lambda^2}\right)} \right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

11. The process of claim 2 which is governed by the algorithm;

$$g(\theta) = p(\Gamma)\left\{e^{\left(-\frac{2}{3}\frac{KT\theta\left[8\pi n^2 \sin^2\left[\frac{\alpha}{2}\right]\right]}{3\eta R\lambda^2}\right)}\right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

12. The process of claim 1 controlled by means of electronic data processing program software.

13. The process of claim 2 controlled by means of electronic data processing program software.

14. The process of claim 3 controlled by means of electronic data processing program software.

15. The process of claim 4 controlled by means of electronic data processing program software.

16. The process of claim 12 governed by the algorithm:

$$g(\theta) = p(\Gamma)\left\{e^{\left(-\frac{2}{3}\frac{KT\theta\left[8\pi n^2 \sin^2\left[\frac{\alpha}{2}\right]\right]}{3\eta R\lambda^2}\right)}\right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

17. The process of claim 13 governed by the algorithm:

$$g(\theta) = p(\Gamma)\left\{e^{\left(-\frac{2}{3}\frac{KT\theta\left[8\pi n^2 \sin^2\left[\frac{\alpha}{2}\right]\right]}{3\eta R\lambda^2}\right)}\right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

18. The process of claim 14 governed by the algorithm:

$$g(\theta) = p(\Gamma)\left\{e^{\left(-\frac{2}{3}\frac{KT\theta\left[8\pi n^2 \sin^2\left[\frac{\alpha}{2}\right]\right]}{3\eta R\lambda^2}\right)}\right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

19. The process of claim 15 governed by the algorithm:

$$g(\theta) = p(\Gamma)\left\{e^{\left(-\frac{2}{3}\frac{KT\theta\left[8\pi n^2 \sin^2\left[\frac{\alpha}{2}\right]\right]}{3\eta R\lambda^2}\right)}\right\}$$

wherein the symbol p(Γ) is decay rate distribution; the symbol Γ is decay rate; the symbol g(θ) is the normalized intensity correlation function; the symbol λ is the scattered light wave length; the symbol α is the scattering angle; the symbol η is the solvent viscosity; the symbol θ is time; n is the refractive index; K is the Boltzmann constant; and T is temperature in degrees Kelvin at the location where the endpoint is determined in the light scattering apparatus.

* * * * *